May 11, 1965 W. E. SILVA Plant Pat. 2,512
APPLE TREE
Filed Dec. 3, 1963
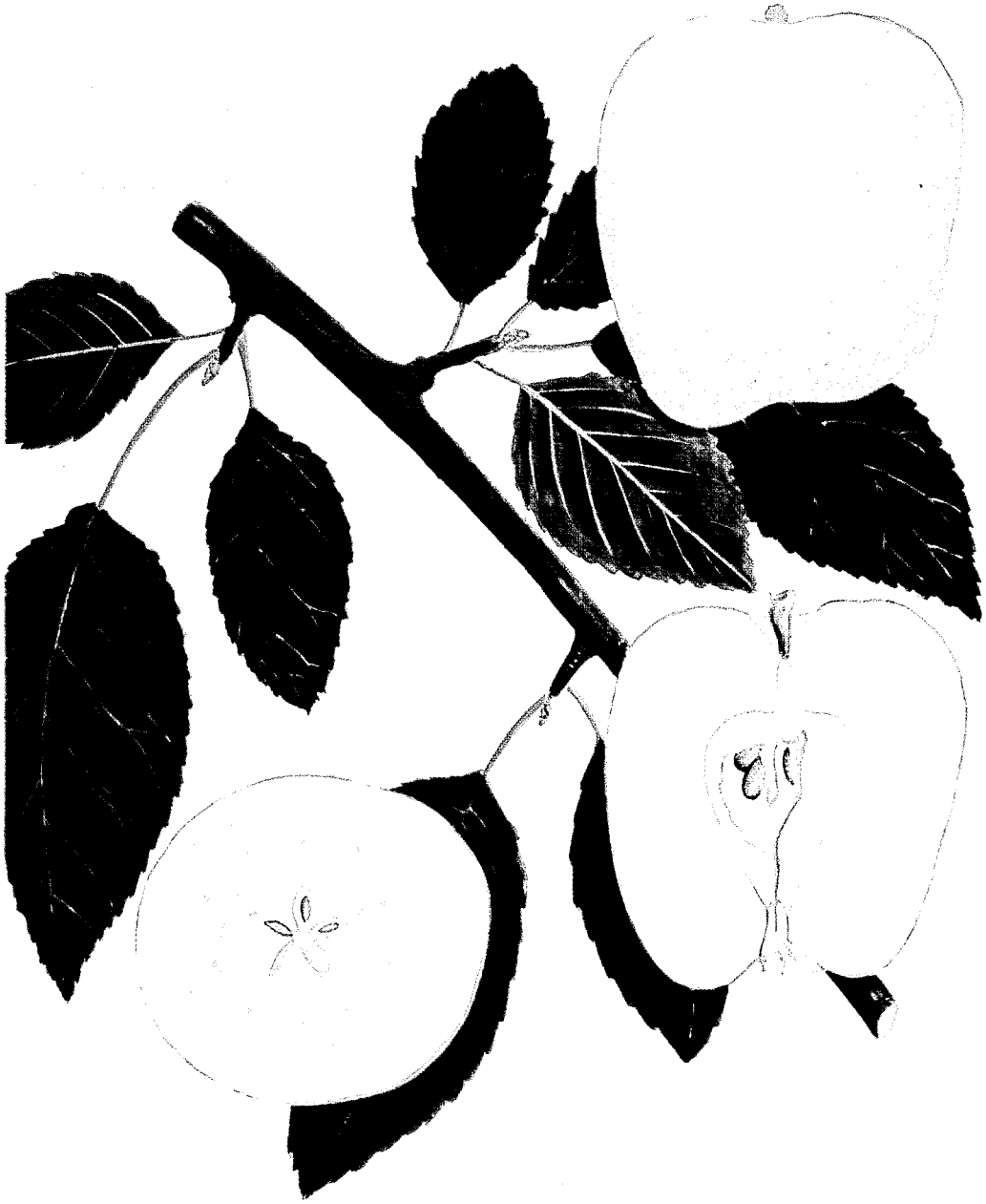
WITNESS
Samuel H. Frost
INVENTOR
WILLIAM E. SILVA.
by Rummler & Snow
ATTYS.

United States Patent Office

Plant Pat. 2,512
Patented May 11, 1965

2,512
APPLE TREE

William E. Silva, 408 Water Trough Road,
Sebastopol, Calif.

Filed Dec. 3, 1963, Ser. No. 327,854
1 Claim. (Cl. Plt.—34)

This invention is of a new and distinct variety of apple tree which was discovered by me, on my breeding grounds at Sebastopol, California, in the course of my work in attempting to develop an improved apple having better keeping qualities for storage and a high sugar and total solids content.

The fruit of this new variety is similar to the Golden Delicious in color and form, as might be expected from the parentage of the plant, but is particularly distinguished by its extraordinary pineapple-like flavor and aroma as well as it high sugar content. The pineapple-like flavor, and hence the delicious eating quality of this apple, led to further investigation of this variety and the discovery of its herein described additional advantages with the result that propagation for commercial purposes was decided upon.

My present new variety developed from a seedling produced by cross breeding Gravenstein, as the seed parent, with Golden Delicious as the pollen parent, both of these varieties being unpatented. This new variety has been observed to be a very fast and vigorously growing tree, with upright branches growing from a thick trunk. Its foliage is very heavy and vigorous, with large heavy leaves and many spur limbs of 4 to 8 inches in length, and the fruit grows on the main branches as well as on the spur limbs or branches.

The new variety of apple tree flowers in April, in California, at about the same time as Golden Delicious, with very large blossoms of a creamy pink color. The tree comes into full bloom during the last week in April and is a very heavy producer of fruit, which ripens during the second week in October, about three weeks ahead of Golden Delicious. The new variety has also been observed, at Sebastopol, California, to be free of mildew and the diseases that attack other varieties of apple trees in the Sabastopol, California, area.

The fruit of this new variety has excellent keeping qualities for winter storage and a relatively high total sugar and solid content of 18.2%. The flesh is crunchy and firm, like Golden Delicious, and the strong aroma and pineapple flavor, coupled with the high sugar content, makes this apple particularly desirable for substantially all uses, especially cooking or canning. Also the strong pineapple flavor is a very dominant and favorable factor in the choice of this apple for use in pasteries and pies.

The accompanying drawing, in full color, shows typical examples of the fruit and foliage of my new variety of apple tree, the fruit being shown in both axial and transverse cross section as well as in elevation; and the following is a more detailed description of the new variety with the color designations according to Maerz and Paul's "A Dictionary of Color."

*The tree*

Origin: Seedling.
*Seed parent.*—Gravenstein (unpatented).
*Pollen patent.*—Golden Delicious (unpatented).
Classification: Hybrid.
Growth habit: Vigorous, upright, hardy and very fast.
Height: Over fourteen feet.
Trunk: Thick and heavy, from ground up.
Branches: Upright, with many fruiting spur limbs 4 to 8 inches in length growing on main branches as well as branching limbs. Color—Plate 23, C–6.

Foliage: Very heavy and vigorous.
*Leaves.*—Abundant and large—3½ to 5 inches long and 2¼ to 2¾ inches wide. Shape—ovate-deltoid, serrated margins. Color: upper side—Plate 23, L–8 to L10; under side—Plate 22, I–4 to I–6; petiole and mid rib—Plate 19, H–2 with overtone of Plate 12, H–10.
*Fruiting spurs.*—Abundant—4 to 8 inches long.

*Flowers*

Blooms: About mid-April in northern California, with large blossoms having a creamy pink color.

*The fruit*

Shape: Oblong-annular, with flattened ends, slightly smaller diameter at base.
Size: About 2½ inches in diameter and about 3 inches high.
Color: Over-all yellow—Plate 9, L–2, with a warm overtone of Plate 9, L–7; often with a blush of pink on the sunny side.
Stem: About ⅜ inch long.
*Color.*—Plate 12, J–8.
*Cavity.*—About ½ inch wide and approx. ⅜ inch deep.
*Basin.*—About ¾ inch wide and approx. 5/16 inch deep.
Calyx:
*Eye.*—About ¼ inch in diameter.
*Tubes.*—Approx. ⅝ inch long, and about 3/16 to ⅛ inch in diameter.
*Color.*—Plate 13, H–3 to H–6.
Core:
*Seed cavity.*—⅞ inch long, ⅝ inch wide. Color—Plate 11, K–3.
*Seeds.*—About 3/16 inch wide, 5/16 inch long and 1/16 inch thick. Color—Plate 7, H–12.
Flesh: Firm in texture, juicy and crunchy when eaten.
*Flavor.*—Strong, very rich pineapple-like flavor.
*Aroma.*—Very pleasant and predominant.
*Color.*—Slightly off-white.
*Total solids and sugar content.*—18.2%.
Maturity season: Second week in October.
Keeping quality: Very good through entire winter season.
Use: Excellent eating apple. Very good for cooking and canning.

In particular my new variety of yellow apple is distinguished by its predominant pineapple-like flavor and aroma and by its relatively high sugar and solids content. It has the advantages of ripening about three weeks prior to Golden Delicious and a very good keeping quality for winter storage purposes; and is particularly good for both eating, cooking, and canning purposes because of its pleasing taste and aroma which persist through the cooking process. The plant is distinguished by its vigorous and rapid growth and by its high production of fruit.

Having now described my new variety of apple tree, I claim:

A new and distinct variety of apple tree, substantially as shown and described, particularly characterized as to novelty by the predominant pineapple-like flavor of its golden yellow fruit, by the early maturity season for its fruit, by the persistent pleasing aroma of the fruit as fresh fruit and throughout cooking and canning procedures, and by the relatively high content of sugar and solids in the ripened fruit.

No references cited.

ABRAHAM G. STONE, *Primary Examiner.*